(12) United States Patent
Chang et al.

(10) Patent No.: US 8,306,597 B2
(45) Date of Patent: Nov. 6, 2012

(54) PHYSIOLOGICAL SIGNAL SENSING DEVICE

(75) Inventors: Wen-Ying Chang, Taoyuan County (TW); Cheng-Hung Chang, Taichung (TW)

(73) Assignee: Industrial Technology Research Institute, Hsinchu (TW)

( * ) Notice: Subject to any disclaimer, the term of this patent is extended or adjusted under 35 U.S.C. 154(b) by 429 days.

(21) Appl. No.: 12/721,513

(22) Filed: Mar. 10, 2010

(65) Prior Publication Data

US 2011/0118574 A1 May 19, 2011

(30) Foreign Application Priority Data

Nov. 16, 2009 (TW) .............................. 98138782 A

(51) Int. Cl.
 *A61B 5/1455* (2006.01)
 *A61B 6/00* (2006.01)
(52) U.S. Cl. ...................................... 600/324; 600/476
(58) Field of Classification Search .......... 600/322–327, 600/476
See application file for complete search history.

(56) References Cited

U.S. PATENT DOCUMENTS

| 4,730,622 | A | 3/1988 | Cohen |
| 7,209,605 | B2 | 4/2007 | Cantin et al. |
| 7,583,865 | B2 | 9/2009 | Berger |
| 7,753,902 | B1 * | 7/2010 | Mansour et al. ............. 604/541 |
| 2002/0010500 | A1 | 1/2002 | Chen |
| 2008/0058908 | A1 | 3/2008 | Bornstein |
| 2011/0118574 | A1 * | 5/2011 | Chang et al. ................. 600/324 |

FOREIGN PATENT DOCUMENTS

| TW | 521147 | 2/2003 |
| TW | 200724091 | 7/2007 |

OTHER PUBLICATIONS

Taiwan Patent Office, Office Action, Patent Application Serial No. 098138782, Jul. 9, 2012, Taiwan.

* cited by examiner

*Primary Examiner* — W. B. Perkey

(57) ABSTRACT

A physiological signal sensing device for examination of human is provided. The physiological signal sensing device includes a light emitting fiber and a light receiving fiber. The light emitting fiber includes a plurality of light emitting portions, wherein the light emitting fiber provides a plurality of sensing beams, and the sensing beams are respectively emitted through the light emitting portions. The light receiving fiber includes a plurality of light receiving portions. The light receiving fiber corresponds to the light emitting fiber. The sensing beams are emitted through the light emitting portions, reflected or refracted by the human. And then the sensing beams are received by the light receiving portions.

27 Claims, 8 Drawing Sheets

PHYSIOLOGICAL SIGNAL SENSING DEVICE

CROSS REFERENCE TO RELATED APPLICATIONS

This Application claims priority of Taiwan Patent Application No. 098138782, filed on Nov. 16, 2009, the entirety of which is incorporated by reference herein.

BACKGROUND OF THE INVENTION

1. Field of the Invention

The present invention relates to a physiological signal sensing device, and particularly relates to a physiological signal sensing device examination of a human with multi-point detection.

2. Description of the Related Art

Conventionally, a human heart pulse, blood oxygen level and blood sugar level are detected by optical detection devices with a single light source (for example, a laser or a light emitting diode) and a single light receiver, thereby providing single point detection results. To provide multi-point detection, the amount of light sources and light receivers used are increased, thus increasing costs.

U.S. Pat. No. 4,730,622 "pressure and oxygen saturation catheter" and U.S. Pat. No. 7,209,605 "packaged optical sensors on the side of optical fibers" disclose a method to detect a human heart pulse, blood oxygen level and blood sugar level with a single optical fiber. However, the optical fiber is very fragile and easily breaks when contacting skin of a patient.

BRIEF SUMMARY OF THE INVENTION

A detailed description is given in the following embodiments with reference to the accompanying drawings.

A physiological signal sensing device for examination of a human is provided. The physiological signal sensing device includes a light emitting fiber, a light receiving fiber and a soft carrier. The light emitting fiber includes a plurality of light emitting portions, wherein the light emitting fiber provides a plurality of sensing beams, and the sensing beams are respectively emitted through the light emitting portions. The light receiving fiber includes a plurality of light receiving portions. The light receiving fiber corresponds to the light emitting fiber. The sensing beams are emitted through the light emitting portions, reflected or refracted by the Human body (tissue or skin). And then the sensing beams are received by the light receiving portions. The light emitting fiber and the light receiving fiber are disposed on the soft carrier side by side.

The physiological signal sensing device of the embodiment can be bent to be attached on a surface of the skin. In the embodiment of the invention, the soft carrier increases structural strength and flexibility of the light emitting fiber and the light receiving fiber. The light emitting fiber and the light receiving fiber are thus prevented from breaking when bent. As well, the soft carrier restricts the light emitting and receiving directions of the fibers.

BRIEF DESCRIPTION OF THE DRAWINGS

The present invention can be more fully understood by reading the subsequent detailed description and examples with references made to the accompanying drawings, wherein:

FIG. 3a-1 is a sectional view along direction A-A of FIG. 1;
FIG. 3a-2 is an enlarged view of portion 3a-2 of FIG. 3a-1;
FIG. 3b-1 is a sectional view along direction B-B of FIG. 1;
FIG. 3b-2 is an enlarged view of portion 3b-2 of FIG. 3b-1.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
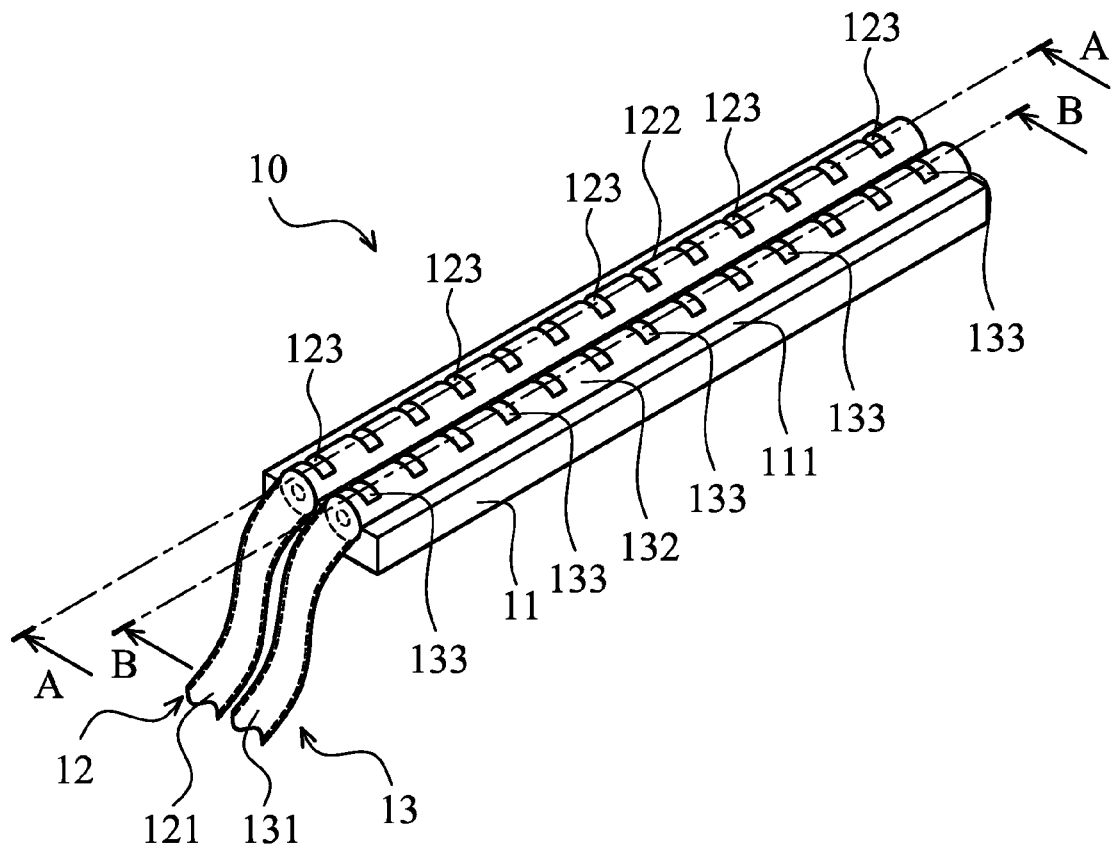
FIG. 1 shows a physiological signal sensing device of a first embodiment of the invention.

FIG. 1 shows a physiological signal sensing device 10 of a first embodiment of the invention for examination of a human. The physiological signal sensing device 10 comprises a light emitting fiber 12, a light receiving fiber 13 and a soft carrier 11.

The light emitting fiber 12 comprises a first coupling section 121, an emitting section 122 and a plurality of light emitting portions 123. The first coupling section 121 is connected to the emitting section 122. The light emitting portions 123 are formed on the emitting section 122. The light emitting fiber 12 provides a plurality of sensing beams, and the sensing beams are respectively emitted through the light emitting portions 123.

The light receiving fiber 13 comprises a second coupling section 131, a receiving section 132 and a plurality of light receiving portions 133. The second coupling section 131 is connected to the receiving section 132. The light receiving portions 133 are formed on the receiving section 132. The sensing beams are emitted through the light emitting portions 123, reflected or refracted by the human tissue, and are received by the light receiving portions 133. The light receiving fiber 13 and the light emitting fiber 12 are disposed on the soft carrier 11 side by side. The light receiving fiber 13 is parallel to the light emitting fiber 12. The light emitting portions 123 are side by side corresponding to the light receiving portions 133. The embodiment does not limit the invention, which can be modified according to practical requirements.

Figure 2:
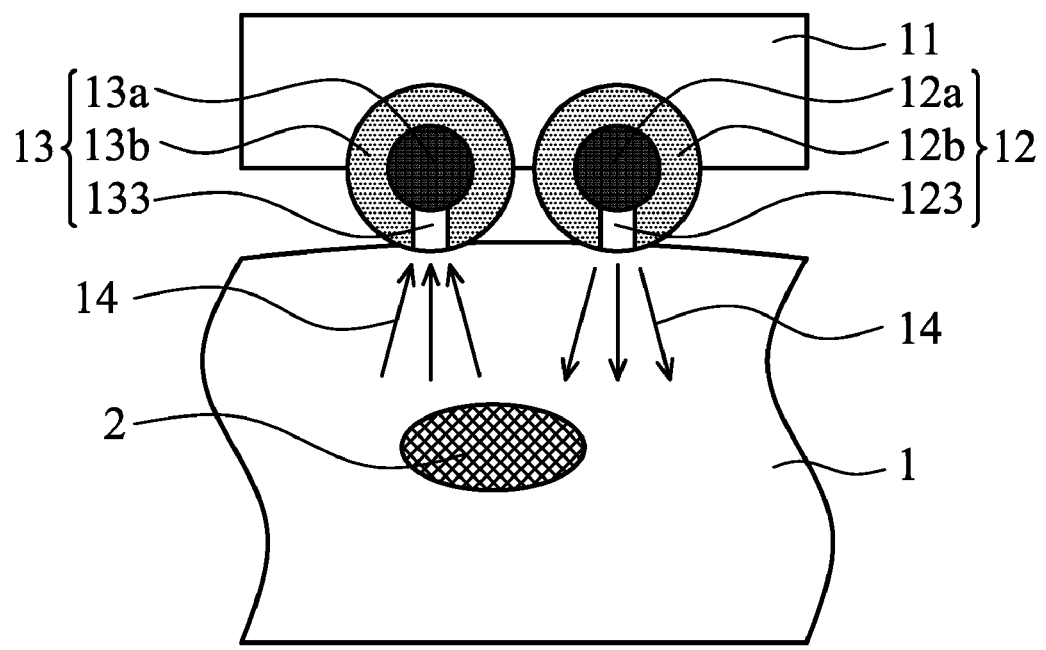
FIG. 2 shows the physiological signal sensing device of the first embodiment during examination of a human physiological signal.

FIG. 2 shows the physiological signal sensing device 10 of the first embodiment during examination of a human. In this embodiment, the sensing target is, but not limited to, a human. However, the application of the invention is not limited thereto. As shown in FIG. 2, the sensing beams 14 are emitted through the light emitting portions 123, reflected or refracted by skin and tissue 1 or blood vessel 2, and are received by the light receiving portion 133. The physiological signal sensing device 10 can be attached to human skin to detect human heart-pulse/blood-oxygen/blood-sugar signals. The light emitting portions 123 have a light emitting direction, the light receiving portions 133 have a light receiving direction, and the light emitting portions and the light receiving portions are facing the human body surface.

Figures 1, 3A:
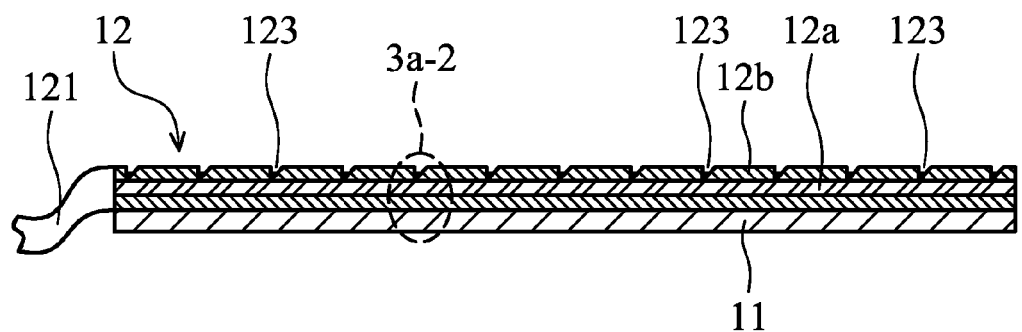
Figures 2, 3A:
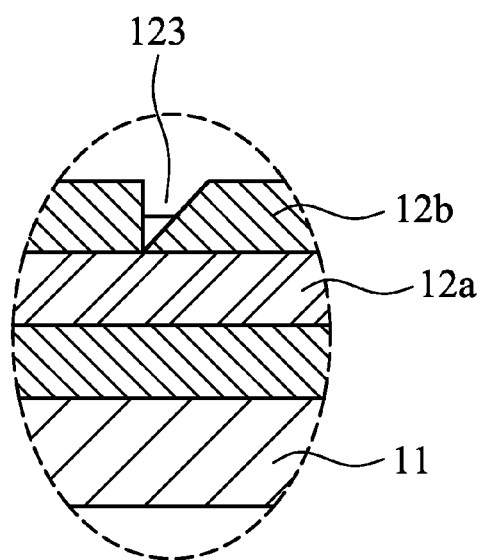

FIG. 3a-1 is a sectional view along direction A-A of FIG. 1, and FIG. 3a-2 is an enlarged view of portion 3a-2 of FIG. 3a-1. With reference to FIGS. 2, 3a-1 and 3a-2, the light emitting fiber 12 has a first core 12a and a first cover 12b. The first cover 12b covers the first core 12a. The light emitting portions 123 are formed on the first fiber cover 12b, a sensing light (not shows) travels in the first core 12a, and the sensing light is emitted through the light emitting portions 123 and transmitted as sensing beams 14.

Figures 1, 3B:
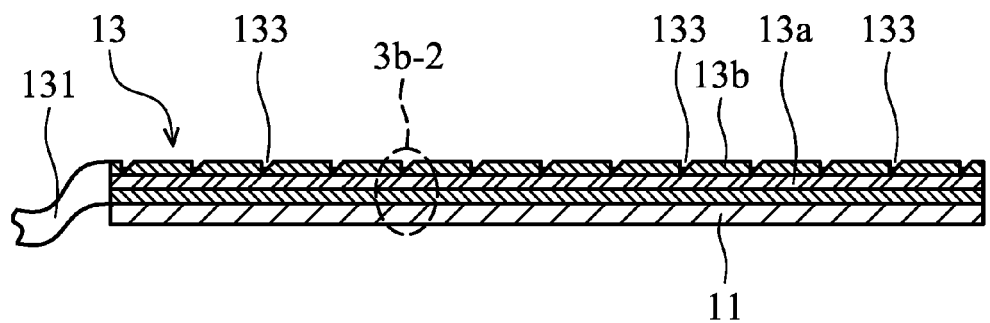
Figures 2, 3B:
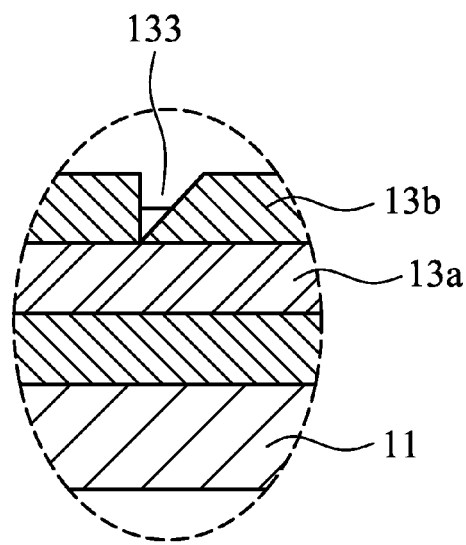

FIG. 3b-1 is a sectional view along direction B-B of FIG. 1, and FIG. 3b-2 is an enlarged view of portion 3b-2 of FIG. 3b-1. With reference to FIGS. 2, 3b-1 and 3b-2, the light receiving fiber 13 has a second core 13a and a second cover 13b. The second cover 13b covers the second core 13a. The light receiving portions 133 are formed on the second fiber cover 13b, and the sensing beams 14 enter the second core 13a through the light receiving portions 133 and travel in the second core 13a.

In one embodiment, the light emitting fiber 12 and the light receiving fiber 13 are multi-wavelength optical fibers. The light emitting portions 123 and the light receiving portions 133 are grooves. The light emitting portions 123 and the light receiving portions 133 can be formed by photolithography or other micro machining methods. However, the invention is not limited thereto.

Figure 4:
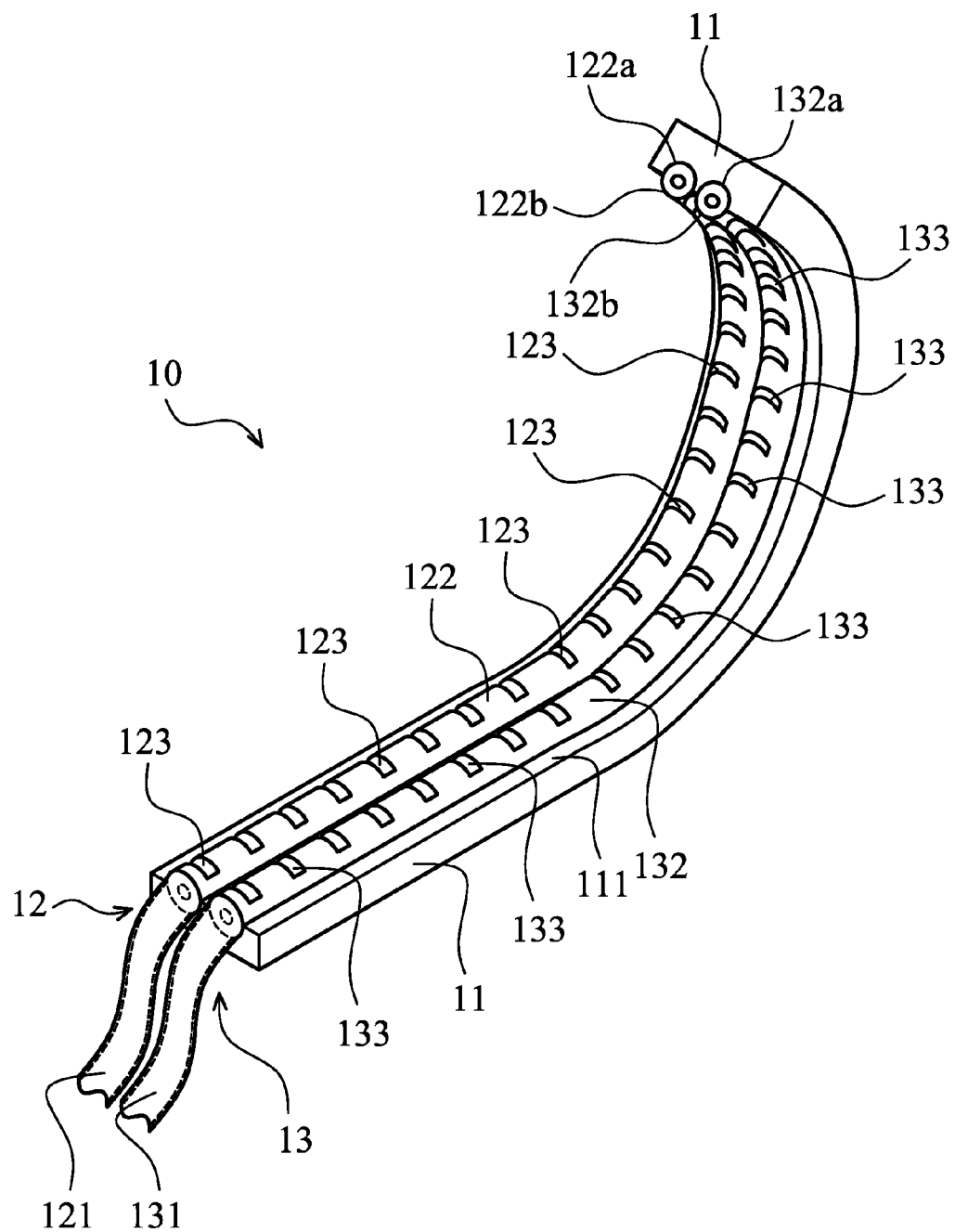
FIG. 4 is a perspective view of the physiological signal sensing device of the first embodiment when the physiological signal sensing device is curved.

With reference to FIGS. 1 and 4, the light emitting fiber 12 and the light receiving fiber 13 are partially embedded in the soft carrier 11. The light emitting fiber 12 has a first protrusion 122b and a first embedded portion 122a. The first protrusion 122b protrudes on a surface 111 of the soft carrier 11. The light emitting portion 123 are formed in the first protrusion 122b. The first embedded portion 122a is embedded in the soft carrier 11.

The light receiving fiber 13 has a second protrusion 132b and a second embedded portion 132a. The second protrusion 132b protrudes on the surface 111 of the soft carrier 11. The light receiving portion 133 are formed in the second protrusion 132b. The second embedded portion 132a is embedded in the soft carrier 11.

The soft carrier 11 can be made of polyurethane, polyimide or silica gel, which can be transparent or opaque. However, the invention is not limited thereto. In one embodiment, a total reflection layer (not shown) can be formed on a surface of the soft carrier contacting the first embedded portion and the second embedded portion.

As shown in FIG. 4, the physiological signal sensing device of the embodiment can be bent to be attached on a surface of the human body. In the embodiment of the invention, the soft carrier 11 increases structural strength and flexibility of the light emitting fiber 12 and the light receiving fiber 13. The light emitting fiber 12 and the light receiving fiber 13 are thus prevented from breaking when bent. As well, the soft carrier restricts the light emitting and receiving directions of the fibers.

Figure 5:
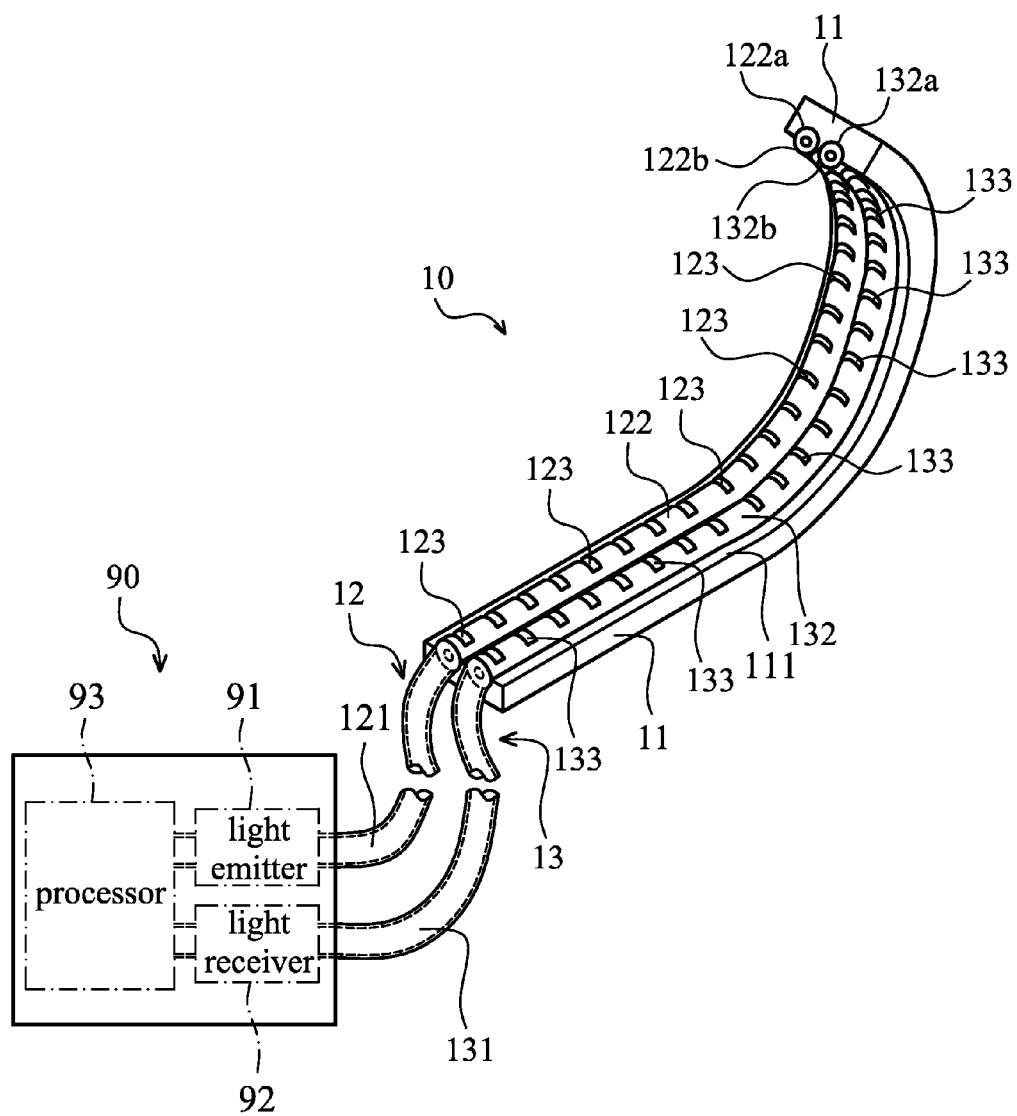
FIG. 5 shows the physiological signal sensing device utilized with a heart pulse/blood-oxygen/blood-sugar signal processing unit.

With reference to FIG. 5, the physiological signal sensing device 10 can be utilized with a heart pulse/blood-oxygen/blood-sugar signal processing unit 90. The heart pulse/blood-oxygen/blood-sugar signal processing unit 90 has a light emitter 91, a light receiver 92 and a processor 93. The light emitting fiber 12 is coupled to the light emitter 91. The light receiving fiber 13 is coupled to the light receiver 92. During an examination, the physiological signal sensing device 10 is attached to human skin, and the light emitted fiber 12 and the light receiving fiber 13 contacts the human skin. Then, the light emitter 91 sends a single-wave or multi-wave sensing light into the light emitting fiber 12, and the sensing light is emitted through the light emitting portions 123 for multi-point detection. The sensing light is partially abstracted by skin tissue and partially reflected or refracted by human tissues. The sensing light reflected/refracted by human tissue enter the light receiving portions 133 of the light receiving fiber 13, and is transmitted to the light receiver 92. Finally, the processor 93 analyses the heart pulse/blood-oxygen/blood-sugar signal. The embodiment of the invention utilizes the light emitting portions 123 and the light receiving portions 133 to provide multi-point light emitting/receiving function. For similar functions provided by conventional art, the number of light sources can be reduced and costs decreased.

Figure 6:
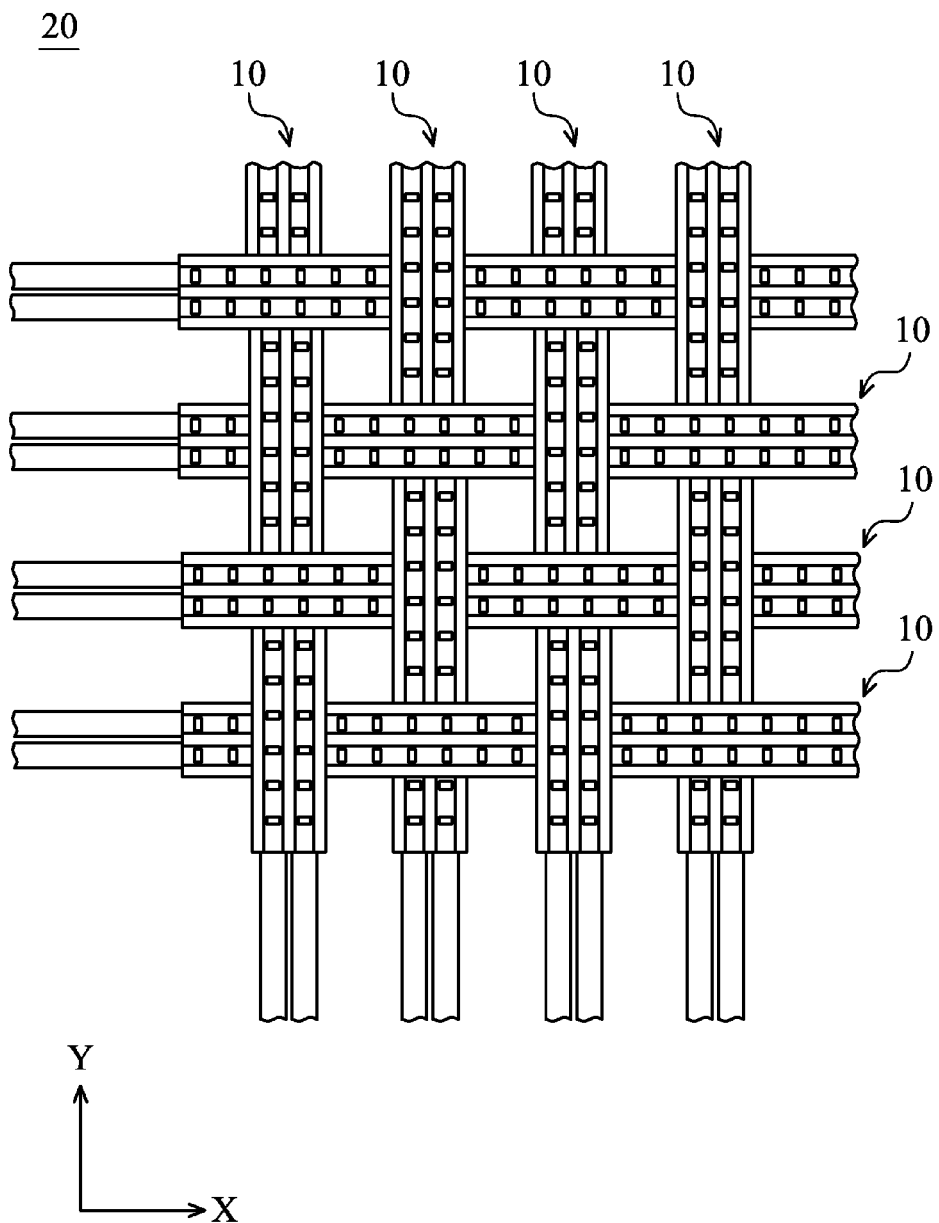
FIG. 6 shows a physiological signal sensing module of an embodiment of the invention.

FIG. 6 shows a physiological signal sensing module 20 of an embodiment of the invention. The physiological signal sensing module 20 comprises a plurality of physiological signal sensing devices 10, wherein the physiological signal sensing devices 10 are arranged along a first direction X and a second direction Y, and the physiological signal sensing devices 10 are interlaced to be a reticular structure. The first direction X is perpendicular to the second direction Y. In this embodiment, the light emitting portions and the light receiving portions are arranged in a matrix. In this embodiment, the detection points of the physiological signal sensing module can be easily positioned, and detection accuracy may be improved when compared to conventional methods.

Figure 7:
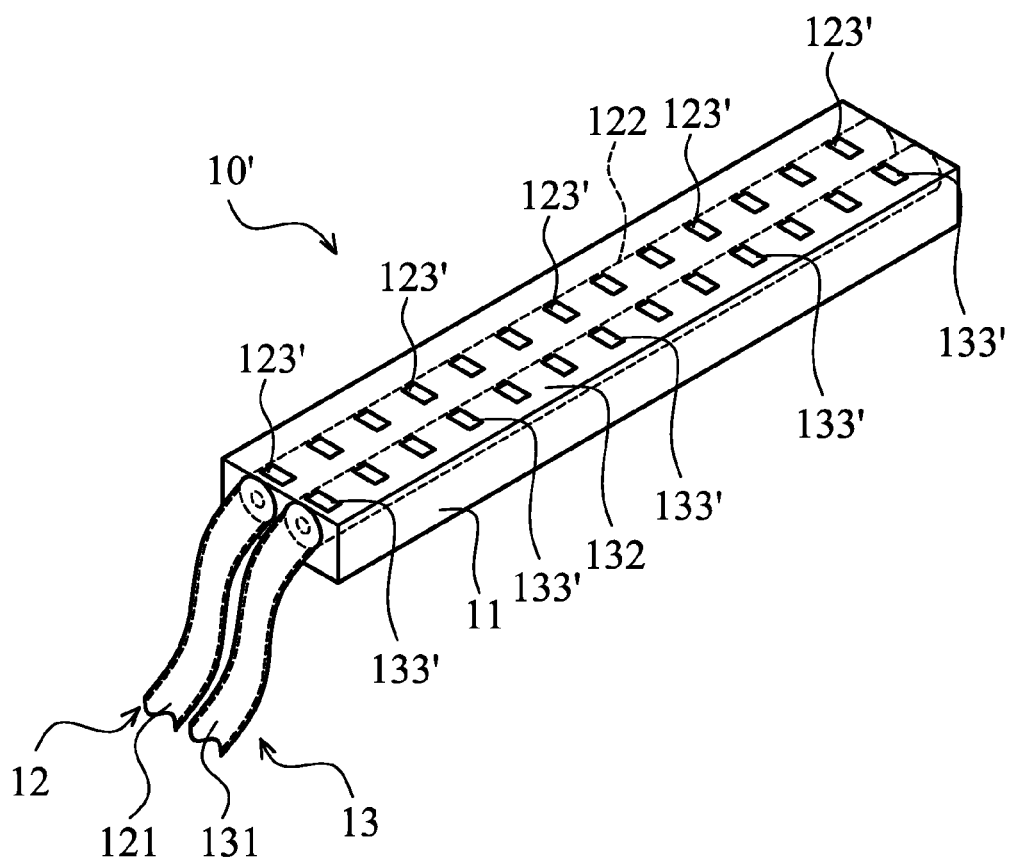
FIG. 7 shows a physiological signal sensing device of a second embodiment of the invention.

FIG. 7 shows a physiological signal sensing device 10' of a second embodiment of the invention. The physiological signal sensing device 10' comprises a light emitting fiber 12, a light receiving fiber 13 and a soft carrier 11. The main characteristic of the second embodiment of the invention is that the light emitting fiber 12 and the light receiving fiber 13 are embedded in the soft carrier 11. The soft carrier 11 has a plurality of light emitting portions 123' and a plurality of light receiving portions 133'. The light emitting fiber 12 is embedded in the soft carrier 11 corresponding to the light emitting portions 123'. The light emitting fiber 12 provides a plurality of sensing beams, and the sensing beams are emitted through the light emitting portions 123'. The light receiving fiber 13 is embedded in the soft carrier 11 corresponding to the light receiving portions 133'. The sensing beams are emitted through the light emitting portions 123', reflected/refracted by the human body, received by the light receiving portions 133', and is transmitted by the light receiving fiber 13. In this embodiment, the light emitting fiber 12 and the light receiving fiber 13 can have transparent fiber covers, or have no fiber covers.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A physiological signal sensing module for examination of a human, comprising:
   a plurality of physiological signal sensing devices, wherein the physiological signal sensing devices are arranged along a first direction and a second direction, and the physiological signal sensing devices are interlaced to be a reticular structure, wherein each of the physiological signal sensing devices comprises:
   a light emitting fiber, comprising a plurality of light emitting portions, wherein the light emitting fiber provides a plurality of sensing beams, and the sensing beams are respectively emitted through the light emitting portions;

a light receiving fiber, comprising a plurality of light receiving portions, wherein the light receiving fiber corresponds to the light emitting fiber, and the sensing beams are emitted through the light emitting portions, reflected or refracted by the human, and are received by the light receiving portions; and a soft carrier, wherein the light receiving fiber and the light emitting fiber are disposed on the soft carrier side by side.

2. The physiological signal sensing module as claimed in claim 1, wherein the light receiving fiber and the light emitting fiber are partially embedded in the soft carrier.

3. The physiological signal sensing module as claimed in claim 2, wherein the light emitting fiber has a first protrusion, the first protrusion protrudes on a surface of the soft carrier, and the light emitting portion is formed in the first protrusion.

4. The physiological signal sensing module as claimed in claim 3, wherein the light receiving fiber has a second protrusion, the second protrusion protrudes on the surface of the soft carrier, and the light receiving portion is formed in the second protrusion.

5. The physiological signal sensing device as claimed in claim 1, wherein the soft carrier is made of polyurethane, polyimide or silica gel.

6. The physiological signal sensing module as claimed in claim 1, each physiological signal sensing device further comprising a total reflection layer, wherein the total reflection layer is formed on a surface of the soft carrier contacting the light receiving fiber and the light emitting fiber.

7. The physiological signal sensing module as claimed in claim 1, wherein the light emitting fiber has a first fiber core and a first fiber cover, the first fiber cover covers the first fiber core, the light emitting portions are formed on the first fiber cover, a sensing light travels in the first core, and the sensing light is emitted through the light emitting portions to be the sensing beams.

8. The physiological signal sensing module as claimed in claim 1, wherein the light receiving fiber has a second fiber core and a second fiber cover, the second fiber cover covers the second fiber core, the light receiving portions are formed on the second fiber cover, and the sensing beams enter the second core through the light receiving portions and travel therein.

9. The physiological signal sensing module as claimed in claim 1, wherein the light emitting fiber is a multi-wavelength optical fiber.

10. The physiological signal sensing module as claimed in claim 1, wherein the light receiving fiber is a multi-wavelength optical fiber.

11. The physiological signal sensing module as claimed in claim 1, wherein the light emitting portions are grooves.

12. The physiological signal sensing module as claimed in claim 1, wherein the light receiving portions are grooves.

13. The physiological signal sensing module as claimed in claim 1, wherein the light emitting portions have a light emitting direction, the light receiving portions have a light receiving direction, and the light emitting portions and the light receiving portions are facing the human.

14. The physiological signal sensing module as claimed in claim 1, wherein the light emitting fiber is parallel to the light receiving fiber.

15. The physiological signal sensing module as claimed in claim 1, wherein the light emitting portions are side by side corresponding to the light receiving portions.

16. The physiological signal sensing module as claimed in claim 1, wherein the first direction is perpendicular to the second direction.

17. A physiological signal sensing module for examination of a human, comprising:

a plurality of physiological signal sensing devices, wherein the physiological signal sensing devices are arranged along a first direction and a second direction, and the physiological signal sensing devices are interlaced to be a reticular structure, wherein each of the physiological signal sensing devices comprises:

a soft carrier, comprising a plurality of light emitting portions and a plurality of light receiving portions;

a light emitting fiber, embedded in the soft carrier and corresponding to the light emitting portions, wherein the light emitting fiber provides a plurality of sensing beams, and the sensing beams are respectively emitted through the light emitting portions; and a light receiving fiber, embedded in the soft carrier and corresponding to the light receiving portions, wherein the sensing beams are emitted through the light emitting portions, reflected or refracted by the human, and then the sensing beams are received by the light receiving portions.

18. The physiological signal sensing device as claimed in claim 17, wherein the soft carrier is made of polyurethane, polyimide or silica gel.

19. The physiological signal sensing module as claimed in claim 17, each physiological signal sensing device further comprising a total reflection layer formed on a surface of the soft carrier contacting the light receiving fiber and the light emitting fiber.

20. The physiological signal sensing module as claimed in claim 17, wherein the light emitting fiber is a multi-wavelength optical fiber.

21. The physiological signal sensing module as claimed in claim 17, wherein the light receiving fiber is a multi-wavelength optical fiber.

22. The physiological signal sensing module as claimed in claim 17, wherein the light emitting portions are grooves.

23. The physiological signal sensing module as claimed in claim 17, wherein the light receiving portions are grooves.

24. The physiological signal sensing module as claimed in claim 17, wherein the light emitting portions have a light emitting direction, the light receiving portions have a light receiving direction, and the light emitting portions and the light receiving portions are facing the human.

25. The physiological signal sensing module as claimed in claim 17, wherein the light emitting fiber is parallel to the light receiving fiber.

26. The physiological signal sensing module as claimed in claim 17, wherein the light emitting portions are side by side corresponding to the light receiving portions.

27. The physiological signal sensing module as claimed in claim 17, wherein the first direction is perpendicular to the second direction.

* * * * *